United States Patent [19]
Racanelli et al.

[11] Patent Number: 5,254,536
[45] Date of Patent: Oct. 19, 1993

[54] THERAPEUTIC UTILITY OF PLASMINOGEN ACTIVATOR INHIBITOR-1 TO CONTROL BLEEDING

[75] Inventors: Adrienne L. Racanelli; Thomas M. Reilly, both of Wilmington, Del.

[73] Assignee: The Du Pont Merck Pharmaceutical Company, Wilmington, Del.

[21] Appl. No.: 820,013

[22] Filed: Jan. 10, 1992

[51] Int. Cl.⁵ ............................................. A61K 37/64
[52] U.S. Cl. ........................................ 514/12; 514/21; 530/300; 530/350
[58] Field of Search ................. 514/21, 12, 8; 222/92; 530/300, 350

[56] References Cited

PUBLICATIONS

Stump et al., Semin. Thromb. Hemos., vol. 16, No. 3, pp. 260-273 (1990).
Lijnen et al., Fibrinolysis, vol. 3, pp. 67-77 (1989).
Van Mourik et al., J. Biol. Chem., vol. 259, pp. 14914-14921 (1984).
Colucci et al., J. Clin. Invest., vol. 75, pp. 818-824 (1985).
Almer et al., Thromb. Research, vol. 47, pp. 335-339 (1987).
Hamsten et al., New England J. of Medicine, vol. 313, pp. 1557-1563 (1985).
Wiman et al., J. Lab. Clin. Med., vol. 105, pp. 265-270 (1985).
Colucci et al., J. Clin. Invest., vol. 78, pp. 138-144 (1986).
Ehrlich et al., J. Biol. Chem., vol. 265, pp. 13029-13035 (1990).
Reilly et al., J. Biol. Chem., vol. 265, No. 16, pp. 9570-9574 (1990).
Racanelli et al., Fibr., vol. 4, Suppl. 3, p. 43 (1990).
Vaughan et al., J. Clin. Invest., vol. 84, pp. 586-591 (1989).
Schwartz, Principles of Surgery, Ch. 3, 5th ed., New York, McGraw-Hill (1984).
Stajcic et al., Int. J. Oral Surg., vol. 14, No. 4, pp. 339-345 (1985).
Allingham et al., Arch. Ophthalmol., vol. 105, No. 10, pp. 1421-1423 (1987).
Verstraete, Drugs, vol. 29, pp. 236-261 (1985).
Maurice, Int. Ophthalmol. Clin., vol. 20, pp. 21-30 (1980).
Cramer et al., Blood, vol. 77, No. 4, pp. 694-699 (1991).
Coleman et al., J. Biol. Chem., vol. 257, pp. 4260-4264 (1982).
Kruithof et al., Thromb. Haemostasis, vol. 59, pp. 7-12 (1988).
Booth et al., Eur. J. Biochem., vol. 165, pp. 595-600 (1987).
Andreasen et al., J. Biol. Chem., vol. 261, pp. 7644-7651 (1986).
Zeheb et al., Thromb. Haemostasis, vol. 58, pp. 1017-1023 (1987).
Hekman et al., J. Biol. Chem., vol. 260, pp. 11581-11587 (1985).
Lambers et al., J. Biol. Chem., vol. 262, pp. 17492-17496 (1987).
Ginsburg et al., J. Clin. Invest., vol. 78, pp. 1673-1680 (1986).
Ny et al., Proc. Natl. Acad. Sci. U.S.A., vol. 83, pp. 6776-6781 (1986).
Pannekoek et al., EMBO J., vol. 5, pp. 2539-2544 (1986).

(List continued on next page.)

Primary Examiner—Howard E. Schain
Assistant Examiner—P. Lynn Touzeau
Attorney, Agent, or Firm—Suzanne E. Miller; Blair Q. Ferguson

[57] ABSTRACT

Pharmaceutical compositions for controlling, by topical administration, localized bleeding in a patient, the composition comprising active PAI-1 protein in an amount effective to control the localized bleeding when topically administered, and a vehicle suitable for the topical administration, as well as methods and kits employing the same, are disclosed.

4 Claims, No Drawings

OTHER PUBLICATIONS

Wun et al., *FEBS Lett.*, vol. 210, pp. 11–16 (1987).
Alessi et al., *Eur. J. Biochem.*, vol. 175, pp. 531–540 (1988).
Andreasen et al., *FEBS Lett.*, vol. 209, pp. 213–218 (1986).
Sisk et al., *Gene (Amst.)*, vol. 96, pp. 305–309 (1990).
Remington's *Pharmaecutical Sciences*, Gennaro, A. R., ed., Mack Publishing Co., Easton, Pa. (1985).
*The United States Pharmacopeia*—The National Formulary, 22nd Revision, Mack Printing Company, Easton Pa. (1990).
McFarlane, *Plas. and Reconstr. Surg.*, vol. 35, No. 2, pp. 177–182 (1965).
Coleman, *J. Biol. Chem.*, vol. 261, pp. 4352–4357 (1986).
Jasani et al., *Lancet*, vol. 2, pp. 332–333 (1977).
Awe et al., *Surgical Bleeding*, Ulin, A. W. and Gollub, S. S., eds., pp. 427–431, New York, McGraw Hill (1966).
Seegers et al., *Proc. Soc. Exp. Biol. Med.*, vol. 56, pp. 72–77 (1944).

THERAPEUTIC UTILITY OF PLASMINOGEN ACTIVATOR INHIBITOR-1 TO CONTROL BLEEDING

BACKGROUND OF THE INVENTION

In order to maintain normal hemostasis, a delicate balance between activators of fibrinolysis, such as tissue plasminogen activator (tPA) and urokinase (uPA), and inhibitors of fibrinolysis, such as $\alpha_2$-antiplasmin, $\alpha_2$-macroglobulin, and plasminogen activator inhibitor-1 (PAI-1), must be achieved. Stump et al., Semin. Thromb. Hemos., Vol. 16, No. 3. pp. 260–273 (1990); Lijnen et al., Fibrinolysis, Vol. 3, pp. 67–77 (1989). Much work has been carried out in an attempt to understand the precise biological role and balance of each of these activators and inhibitors in various physiological and pathophysiological states, and to fashion therapeutics useful in achieving or maintaining the normal hemostatic state. Despite this intensive effort, a great deal still remains to be understood.

Some researchers in this field have focused on understanding the role of the protein plasminogen activator inhibitor-1 (PAI-1). PAI-1 is believed to be the principal physiological regulator of tPA, serving as a specific, fast-acting inhibitor of the serine protease tPA, as well as an inhibitor of uPA. It has been found that PAI-1 is a protein of a molecular weight of about 50,000 which binds to tPA in a 1:1 complex and inactivates it. Van Mourik et al., J. Biol. Chem., Vol. 259, pp. 14914–14921 (1984); Colucci et al., J. Clin. Invest., Vol. 75, pp. 818–824 (1985); Almer et al., Thromb. Research, Vol. 47, pp. 335–339 (1987). Several clinical studies suggest that elevated levels of PAI-1 may contribute to the pathogenesis of various thrombotic disorders, including myocardial infarction, deep vein thrombosis, and disseminated intravascular coagulation, by acting to reduce the net endogenous fibrinolytic capacity. Hamsten et al., New England J. of Medicine, Vol. 313, pp. 1557–1563 (1985); Wiman et al, J. Lab. Clin. Med., Vol 105, pp. 265–270 (1985). In another more recent study, however, it was found that induction of endogenous PAI-1 protein failed to alter thrombolysis caused by an infusion of tPA. Colucci et al., J. Clin. Invest., Vol. 78, pp. 138–144 (1986). The latter experiments suggest that administration of exogenous PAI-1 would not alter fibrinolysis in vivo. Indeed, it has been reported that exogenously administered PAI-1 has no effect on primary bleeding. Further, there is evidence that PAI-1 actually serves to inhibit thrombin, an action which would serve to increase bleeding, if anything. Ehrlich et al., J. Biol. Chem., Vol. 265, pp. 13029–13035 (1990).

Recently, a recombinant form of plasminogen activator inhibitor-1 was produced in active form from *E. coli.* Reilly et al., J. Biol. Chem., Vol. 265, No. 16, pp. 9570–9574 (1990); Davis et al., U.S. Ser. No. 350,264, filed May 11, 1989, entitled "High Level Expression of Functional Human Plasminogen Activator Inhibitor in *E. coli*". This rPAI-1 protein was found to inhibit tPA and uPA with a second order rate constant in the range of $2-5\times 10^{-7}$ $M^{-1}s^{-1}$. The use of this recombinant PAI-1 protein as a therapeutic agent to counteract excessive or inappropriate fibrinolysis was first suggested in the patent application Davis et al., U.S. Ser. No. 350,264, filed May 11, 1989, entitled "High Level Expression of Functional Human Plasminogen Activator Inhibitor in *E. coli*". Further studies have suggested that this recombinant PAI-1 protein, when administered intravenously, is more potent than the antifibrinolytic agent ε-amino caproic acid (EACA) in reversing tPA-induced hemorrhage in a rabbit model Racanelli et al., Fibr., Vol. 4, Suppl. 3, p. 43 (1990). Another recombinant PAI-1 protein purified in an inactive form and activated by treatment with guanidinium hydrochloride was found to reverse tPA-induced bleeding in aspirin-treated rabbits when administered systemically by injection. Vaughan et al., J. Clin. Invest, Vol. 84, pp. 586–591 (1989).

Hemostatic agents suitable for topical administration (rather than oral administration) to control localized bleeding are advantageous in that they are capable of being directly targeted to the area of interest. This potentially allows a more rapid therapeutic response, using lower dosage amounts, while at the same time minimizing the likelihood of side effects characteristic of some systemically administered hemostatic agents. Topically applied hemostatic agents which have been used during surgery to control localized blood loss from primary bleeding have included thrombin, fibrin glue, gelatin sponge, microfibrillar collagen, and oxidized cellulose. Schwartz, Principles of Surgery, Ch. 3, 5th ed., New York, McGraw-Hill (1984).

Several other agents have also been tested topically for hemostatic use. For example, in one study the antifibrinolytic agent EACA was administered locally, systemically, and both locally and systemically, in hemophiliacs undergoing dental extractions and Factor VIII therapy. Stajcic et al., Int. J. Oral Surg., Vol. 14, No. 4, pp. 339–345 (1985). The authors found the therapeutic effects to be unsatisfactory where EACA was only locally applied. Id. at pp. 339 & 340. Later in Allingham et al., Arch. Ophthalmol., Vol. 105, No. 10, pp. 1421–1423 (1988), EACA was employed topically in a rabbit to treat traumatic hyphema, a unique condition of ocular bleeding. In certain applications the antifibrinolytic agent aprotinin has also been applied topically to control bleeding, such as in neurosurgery where aprotinin was employed in combination with artificial fibrin glues. Verstraete, Drugs, Vol. 29, pp 236–261 (1985).

Although some progress has been made in this area, new and/or better agents for topical administration to control localized blood loss are needed. The present invention, which is directed to the first to successful application of the inhibitor PAI-1 topically to control localized bleeding, is directed to this important end.

SUMMARY OF THE INVENTION

In one embodiment, the present invention contemplates pharmaceutical compositions for controlling, by topical administration, localized bleeding in a patient, the composition comprising active PAI-1 protein in an amount effective to control the localized bleeding when topically administered, and a vehicle suitable for the topical administration.

In a further aspect, the subject invention is directed to methods of controlling localized bleeding in a patient, the method comprising topically administering to the patient the pharmaceutical composition described above.

Still further, the present invention is directed to a pharmaceutical kit for controlling, by topical administration, localized bleeding in a patient, the kit comprising a sterile container of the pharmaceutical composition described above. Optionally, the kit may further comprise other conventional pharmaceutical kit components.

DETAILED DESCRIPTION OF THE INVENTION

In accordance with the present invention, PAI-1 protein is employed in controlling bleeding in a patient. By the term "controlling", and variations thereof, as used herein in connection with the control of bleeding, it is meant either partially, substantially or completely arresting (stopping) bleeding. In a preferable embodiment, bleeding is substantially or completely arrested, most preferably completely arrested.

Bleeding which may be controlled in accordance with the subject invention includes localized bleeding. By the phrase "localized bleeding", it is meant bleeding that is confined to a specific area of the patient at or near the surface of the patient's skin (or other outer membranes such as, for example, the mucous membranes of the eye, nose, rectum, etc.). By "near the surface" of the skin (or other outer membranes), it is meant close enough to the surface to be reached by penetration of the topically administered composition of the invention. As those skilled in the art will recognize, penetration may occur through such mechanisms as diffusion or active transport across the skin, mucous membranes and other tissues to reach the area of interest, the degree and rate of penetration being dependent upon such factors as the particular tissues that must be penetrated, the particular vehicles employed, etc. Such factors are well known to those skilled in the art, and are discussed, for example in Maurice, "Factors Influencing the Penetration of Topically Applied Drugs", Int. Ophthalmol. Clin., Vol. 20, pp. 21-30 (1980), and Allingham et al., Arch. Ophthalmol., Vol. 105, No. 10, pp. 1421-1423 (1988), the disclosure of each of which are hereby incorporated herein by reference in their entirety. The specific areas of a patient where localized bleeding may occur may include the areas of a patient's body where surgery has been performed or which has been traumatized by an accident or otherwise. Such localized bleeding may consist of primary bleeding (primary hemorrhage), and/or secondary bleeding (secondary hemorrhage), but in a preferable embodiment the pharmaceutical composition is employed to control secondary bleeding. By "primary bleeding", it is meant that bleeding which occurs immediately after injury to a blood vessel. By "secondary bleeding", it is meant that bleeding which occurs as a result of premature dissolution of the hemostatic plug, a condition which generally will manifest itself between about 2 and about 96 hours following the cessation of primary bleeding, although, of course, this condition may manifest itself at an earlier or later time. The latter condition, that is, secondary bleeding, is often referred to by those skilled in the art as rebleeding.

Thus, in accordance with the present invention, a PAI-1 protein may be employed in combination with a vehicle, such as a vehicle suitable for topical administration, as a pharmaceutical composition.

The phrase "PAI-1 protein", as used herein, denotes the protein commonly referred to as plasminogen activator inhibitor-1, in its natural or recombinant forms. Such natural and recombinant forms of the PAI-1 protein are well known in the art.

For example, PAI-1 may isolated in a natural form from human plasma or endothelial cell culture fluids, as discussed in Coleman et al., J. Biol. Chem., Vol. 257, pp. 4260-4264 (1982), Van Mourik et al., J. Biol. Chem., Vol. 259, pp. 14914-14921 (1984), Kruithof et al., Thromb. Haemostasis, Vol. 59, pp. 7-12 (1988), and Booth et al., Eur. J. Biochem., Vol 165, pp. 595-600 (1987), the disclosures of each of which are hereby incorporated herein by reference in their entirety. PAI-1 may also be isolated from such other natural sources as bovine aortic endothelial cells, HT 1080 human fibrosarcoma cells, and hepatoma tissue culture rat hepatoma cells, as discussed in Van Mourik et al , J. Biol. Chem., Vol. 259, pp. 14914-14921 (1984), Andreasen et al., J. Biol. Chem., Vol. 261, pp. 7644-7651 (1986), and Zeheb et al., Thomb. Haemostasis, Vol. 58, pp. 1017-1023 (1987), the disclosures of each of which are hereby incorporated herein by reference in their entirety. As those skilled in the art are aware, PAI-1 protein isolated from these sources exists chiefly as a latent form with a very low specific activity, as determined in tPA inhibition assays. This latent form can be further activated by treatment with denaturants such as sodium dodecyl sulfate (SDS), guanidium hydrochloride, and urea, or by treatment with negatively-charged phospholipids, as discussed in Hekman et al., J. Biol. Chem., Vol. 260, pp. 11581-11587 (1985), and Lambers et al., J. Biol. Chem., Vol. 262, pp. 17492-17496 (1987), the disclosures of each of which are hereby incorporated herein by reference in their entirety.

The literature is also replete with discussions of recombinant PAI-1 protein production, including, for example, such publications as Ginsburg et al., J. Clin. Invest., Vol 78, pp. 1673-1680 (1986), Ny et al., Proc. Natl. Acad. Sci. U.S.A., Vol. 83, pp. 6776-6781 (1986), Pannekoek et al., EMBO J., Vol. 5, pp. 2539-2544 (1986), Wun et al., FEBS Lett., Vol. 210, pp. 11-16 (1987), Alessi et al., Eur. J. Biochem., Vol. 175, pp. 531-540 (1988), and Andreasen et al., FEBS Lett., Vol. 209, pp. 213-218 (1986), the disclosures of each of which are hereby incorporated herein by reference in their entirety Again, as described above with regard to naturally produced PAI-1 protein, latent recombinant PAI-1 protein forms may be further activated by treatment with denaturants or negatively-charged phospholipids.

A particularly preferred source of PAI-1 protein is the recombinant PAI-1 protein expressed and purified in the manner described in Reilly et al., J. Biol. Chem., Vol. 265, No. 16, pp. 9570-9574 (1990), Sisk et al., Gene (Amst.), Vol. 96, pp. 305-309 (1990), and in the patent application Davis et al., U.S. Ser. No. 350,264, filed May 11, 1989, entitled "High Level Expression of Functional Human Plasminogen Activator Inhibitor in *E. coli*", the disclosures of each of which are hereby incorporated herein by reference in their entirety. In accordance with the protocol described therein, substantial quantities of functionally active, protein are readily expressed and purified. The particular form of PAI-1 described in Reilly et al , J. Biol. Chem., Vol. 265, No. 16, pp. 9570-9574 (1990), Sisk et al., Gene (Amst.), Vol. 96, pp. 305-309 (1990), and the patent application Davis et al., U.S. Ser. No. 350,264, filed May 11, 1989, entitled "High Level Expression of Functional Human Plasminogen Activator Inhibitor in *E. coli*", shall be referred to herein as it is in the latter document, that is, as substantially pure, biologically functional, nonfused *E. coli*-expressed human PAI-1 protein having a specific activity of about 1 unit/ng. By "nonfused", as used in the foregoing phrase, it is meant a PAI-1 protein which is not fused to any linker protein, unlike a number of other forms of recombinant PAI-1 proteins known in the art. By "biologically functional", it is meant a PAI-1 protein that is capable of inhibiting, at least to some degree, the target tPA (that is, the protein is "active"). Further, as defined in the patent application Davis et al., U.S. Ser. No.350,264, filed May 11, 1989, entitled "High Level Expression of Functional Human Plasminogen Activator Inhibitor in *E. coli*", a unit of PAI-1 protein is the amount of protein required to neutralize 1 international unit of tPA in an S2251 chromogenic assay, where the enzymatic activity of tPA to generate plasmin from its plasminogen precursor is measured. The activity of tPA is expressed in IU by comparison with the International Reference Preparation for tPA. Specifically, as described in the patent application Davis et al., U.S. Ser. No. 350,264, filed May 11, 1989, entitled "High Level Expression of Functional Human Plasminogen Activator Inhibitor in *E. coli*", the S2251 assay measures the enzymatic ability of tissue plasminogen activator (tPA) to generate plasmin from its plasminogen precursor by determining the level of amidolytic activity of generated plasmin on the chromogenic substrate D-Val-Leu-Lys-p-nitroanilide (S2251). Thus, in this fashion, the inhibitory activity of PAI-1 is determined. In the S2251 assay employed in the patent application Davis et al., U.S. Ser. No. 350,264, filed May 11, 1989, entitled "High Level Expression of Functional Human Plasminogen Activator Inhibitor in *E. coli*", 50% inhibition of 10 international units (IU) of tPA activity was observed with $2.5 \times 10^{-4}$ mg/ml of natural human PAI-1 and with $5.3 \times 10^{-5}$ mg/ml of substantially pure, biologically functional, nonfused *E. coli*-expressed human PAI-1 protein. The activity of tPA is then expressed in IU by comparison with the International Reference Preparation for tPA. Accounting for an assay volume of 100 μl, it was calculated that 25 ng of human PAI-1 reduces the activity of 10 IU of tPA by one-half. Defining a unit of PAI-1 as the amount of protein needed to neutralize 1 IU of tPA, it was determined the specific activity for the human PAI-1, in terms of units/ng, was 5/25 or 0.2 units/ng. A similar calculation was made with the substantially pure, biologically functional, nonfused *E. coli*-expressed human PAI-1 protein, and yielded a specific activity of approximately 1 unit/ng. The latter PAI-1 protein was, therefore, approximately 5-fold more active than the natural human PAI-1 in this particular assay, and has a specific activity in the S2251 chromogenic assay of about 1 units/ng. Those skilled in the art will recognize that some variation in specific activity, e.g., in the range of ±10%, is to be expected.

Another particularly preferred PAI-1 protein is PAI-1 protein which has been subjected to the process described in Hayman et al., U.S. Ser. No. 671,433, filed Mar. 20, 1991, entitled "Purification of Active and Inactive/Latent Forms of Plasminogen Activator Inhibitor-1", the disclosures of which are hereby incorporated herein by reference in their entirety. In accordance with the protocol set forth in the foregoing patent application, the active form of the PAI-1 protein can be separated from its lower activity inactive/latent form. Specifically, the processes described in the Hayman et al. patent application involve loading a sample containing a mixture of active and inactive/latent forms of PAI-1 on to a cation exchange resin of 10–50 micron particle size, and eluting the active and inactive/latent forms of PAI-1 into separate fractions using a mobile phase buffer with a gradient of increasing ionic strength or increasing pH, or both, under conditions where active and inactive/latent forms of PAI-1 are eluted from the resin in separate fractions. Other processes described therein involve loading a sample containing a mixture of active and inactive/latent forms of PAI-1 on to an anion exchange resin of 10–50 micron particle size, and eluting the active and inactive/latent forms of PAI-1 into separate fractions using a mobile phase buffer with a gradient of increasing ionic strength or decreasing pH, or both, under conditions where active and inactive/latent forms of PAI-1 are eluted from the resin in separate fractions.

As those skilled in the art are aware, PAI-1 protein may also be purchased from various commercial sources, such as, for example, from American Diagnostica Inc. (New York, New York), where natural PAI-1 protein purified from human fibrosarcoma cells is available. The protein available from American Diagnostica protein may be further activated with SDS treatment.

The foregoing described and other known natural and recombinant PAI-1 protein sources and forms, as well as obvious variations thereof, are intended to fall within the ambit of the phrase "PAI-1 protein", as used herein, the critical feature being that the PAI-1 protein employed must be capable of inhibiting to at least some degree the target tPA, such PAI-1 proteins being referred to herein as "active" or "biologically functional". Preferably, the active PAI-1 proteins have a specific activity, calculated using the S2251 chromogenic assay as described above, which is between at least about 0.2 units/ng and about 1.0 units/ng, most preferably at least about 1.0 unit/ng. As those skilled in the art would recognize, if activation of the PAI-1 proteins is required for the PAI-1 protein to become biologically functional, such activation may be carried out either before or after administration, although preferably activation is carried out prior to administration. As discussed above, activation may be carried out by treatment with denaturants or negatively-charged phospholipids.

Regardless of the source or form of PAI-1, it is preferable that the protein employed in the pharmaceutical composition be substantially pure, that is, has less than about 5% impurities. Preferably the protein has less than about 1% impurities, that is, is purified to homogeneity.

In formulating the pharmaceutical compositions of the invention, a vehicle suitable for topical administration may be employed. Such vehicles are well known in the art, and will be readily apparent to one skilled in the art, once armed with the present disclosure. Suitable vehicles include, for example, sodium chloride solution (saline solution; available from Mallinkrodt Chemical Works, St. Louis, Miss.); benzalkonium chloride solution (available from Sterling Drug Inc., New York, N.Y.); ethylenediamine tetraacetic acid (EDTA) disodium solution (available from Aldrich Chemical Co., Inc., Milwaukee, Wis.); dimethyl sulfoxide (DMSO) solution (available from Sigma Chemical Co., St. Louis); polyvinyl alcohol solution (available from Allergan, Irvine, Calif.); hydroxypropyl methylcellulose solution (available from Alcon Laboratories, Fort Worth, Tex.); and carboxypolymethylene gel (available from BF Goodrich Co., Cleveland, Ohio). Other suitable vehicles are described, for example, in Remington's, Pharmaceutical Sciences, Gennaro, A. R., ed., Mack Publishing Co., Easton, Pa. (1985), and in The United States Pharmacopeia—The National Formulary, 22nd Revision, Mack Printing Company, Easton Pa. (1990), the disclosures of each of which are hereby incorporated herein by reference in their entirety.

In carrying out the method of the invention, the patient may be any type of a mammal, but most preferably is a human. Administration may carried out by topically applying the pharmaceutical composition in the area of the patient's body where bleeding is occurring, using standard topical application techniques, such as with the use of soaked gauze, for example, Sorbacel ™ gauze (Hartmann), and/or with an aerosol spray. As those skilled in the art will recognize, other conventional routes of administration may be employed, if desired. The useful dosage to be administered (that is, the amount effective to control the bleeding when administered), will vary depending upon such factors as the particular mammal, the mode of administration, and the area thereof to be treated, as well as the degree of bleeding Typically, dosage is initiated at lower levels and increased until the desired therapeutic effect is achieved By way of guidance, however, generally between about 0.05 and about 1.0 mg/in$^2$, preferably about 0.5 mg/in$^2$, of the PAI-1 protein is administered when topical application is desired. Of course, higher and lower amounts can be employed, the particular dosage to be employed being well within the ambit of one skilled in the art, once armed with the present disclosure. As those skilled in the art will recognize, in carrying out the method of the invention, the pharmaceutical composition can be administered alone or in combination with other therapeutic and/or diagnostic agents, as desired. Other such agents include, for example, thrombin, fibrinogen, microfibrillar collagen, and other conventional topical agents.

Kits useful for therapeutic applications comprising the pharmaceutical composition of the present invention are also within the ambit of the present invention. Specifically, such pharmaceutical kits, which may be employed to control, by topical administration, localized bleeding in a patient, comprise a sterile container of a pharmaceutical composition of the invention. Sterilization of the containers of materials included in the kit may be carried out using conventional sterilization methodology well known to those skilled in the art. The sterile containers of PAI-1 protein and vehicle may comprise separate containers, or one or more multi-part containers (as exemplified by the UNIVIAL two-part container available from Abbott Labs, Chicago, Ill.), as desired. Such kits may further include, if desired, one or more of various conventional pharmaceutical kit components, for example, gauze such as SORBACEL gauze (Hartmann) for use in topically applying the composition of the invention, one or more additional vials for mixing the PAI-1 protein and the vehicle, etc., as will be readily apparent to those skilled in the art. Instructions, either as inserts or as labels, indicating quantities of the PAI-1 protein and vehicle, guidelines for mixing the protein and vehicle, and protocols for administration, may also be included in the kit.

The present invention is further described in the following examples. These examples are not to be construed as limiting the scope of the appended claims.

EXAMPLE 1

Inhibition of Bleeding by Topically Administered PAI-1

To evaluate the ability of topically administered recombinant PAI-1 to inhibit the bleeding during and after surgical procedures, a rat dorsal flap model was utilized. Such dorsal flap models are well known in the art and are described, for example, in McFarlane, Plas. and Reconstr. Surg., Vol. 35, No. 2, pp. 177-182 (1965), the disclosures of which are hereby incorporated herein by reference in their entirety. Rats were anesthetized with pentothal (15 mg/kg) and a Mcfarlane flap was produced on the dorsum of each rat. Topical administration of either saline, recombinant PAI-1 (0.35 mg) (produced as described in the patent application Davis et al., U.S. Ser. No. 350,264, filed May 11, 1989, entitled "High Level Expression of Functional Human Plasminogen Activator Inhibitor in *E. coli*", or thrombin (5000 IU), or both the recombinant PAI-1 (0.35 mg) and thrombin (5000 IU), was given to groups of rats (n = 12 or n = 4). A gauze, soaked in distilled water to lyse the blood cells, was placed under the skin to collect any blood oozing from the wound. The optical density (OD) of the solution at 412 nm was determined at both 2 and 24 hours. The OD measurement is a parameter proportional to blood loss, with the higher the optical density, the greater the blood loss.

Topical administration of recombinant PAI-1 (rPAI-1), as shown in Table 1, resulted in a significant decrease in OD (blood loss) as compared to the control group at 2 hours. Recombinant PAI-1 also caused a greater reduction in blood loss than thrombin (5000 IU). At 24 hours, significant differences between the control and treated groups were observed, however, these differences were less striking at 24 hours than at 2 hours. In addition, no synergistic effect for combined thrombin (5000 IU) and rPAI-1 (0.352 mg) was observed.

TABLE 1

|  | OD at 2 hrs. | OD at 24 hrs. |
| --- | --- | --- |
| Control (n = 12) | 1.8 + 0.5 | 0.6 + 0.13 |
| PAI-1 (0.352 mg) (n = 12) | 0.9 + 0.3* | 0.4 + 0.11* |
| thrombin (5000 IU) (n = 12) | 1.3 + 3.5* | 0.4 + 0.08* |
| PAI-1 (0.352 mg) and thrombin (5000 IU) (n = 4) | 0.9 + 0.2* | 0.42 + 0.5* |

The gauze was removed from the wound site and soaked in saline to lyse the red blood cells. Spectroscopic measurements were made at 412 nm, 2 and 24 hours after the injury. Values represent a mean + a standard deviation (SD). The asterisk (*) represents a significant difference from the control group (p<0.05).

What is claimed is:

1. A method of controlling localized bleeding in a patient, said method comprising topically administering to said patient a pharmaceutical composition comprising active PAI-1 protein in an amount effective to control said localized bleeding when topically administered, and a vehicle suitable for said topical administration.

2. A method of controlling localized bleeding in a patient, said method comprising topically administering to said patient a PAI-1 protein wherein said PAI-1 protein is substantially pure, biologically functional, non-fused *E. coli*-expressed human PAI-1 protein having a specific activity of 1 unit/ng.

3. A method of controlling localized bleeding in a patient, said method comprising topically administering to said patient a pharmaceutical composition consisting essentially of active PAI-1 protein in an amount effective to control said localized bleeding when topically administered, and a vehicle suitable for said topical administration.

4. A method according to claim 1 wherein said localized bleeding is primary bleeding.

* * * * *